United States Patent [19]

Kraatz et al.

[11] 4,380,545
[45] Apr. 19, 1983

[54] COMBATING FUNGI WITH TRIAZOLYL-BENZYLOXY-KETONES AND-CARBINOLS

[75] Inventors: Udo Kraatz; Gerhard Jäger, both of Leverkusen; Karl H. Büchel, Burscheid; Paul-Ernst Frohberger, Leverkusen, all of Fed. Rep. of Germany

[73] Assignee: Bayer Aktiengesellschaft, Leverkusen, Fed. Rep. of Germany

[21] Appl. No.: 245,288

[22] Filed: Mar. 19, 1981

[30] Foreign Application Priority Data

Apr. 2, 1980 [DE] Fed. Rep. of Germany ....... 3012824

[51] Int. Cl.³ .................... A01N 43/64; A01N 55/00; C07D 249/08
[52] U.S. Cl. .................... 424/269; 424/232; 424/245; 548/101; 548/262; 568/308; 568/419; 570/127; 570/185
[58] Field of Search ............... 548/101, 262; 424/245, 424/269

[56] References Cited

U.S. PATENT DOCUMENTS 3,912,752 10/1975 Meiser et al. .......... 548/262
3,940,414  2/1976 Krämer et al. .......... 424/273
3,952,002  4/1976 Krämer et al. .......... 548/262
4,002,763  1/1977 Meiser et al. .......... 424/269

*Primary Examiner*—Alton D. Rollins
*Attorney, Agent, or Firm*—Sprung, Horn, Kramer & Woods

[57] ABSTRACT

Triazolyl-benzyloxy-ketones or carbinols of the formula

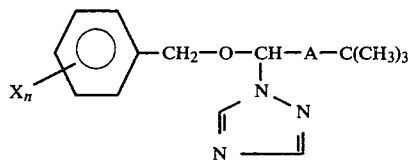

in which
A is a keto group or a CH(OH) group,
X is a halogen atom or an alkyl or halogenoalkyl radical, and
n is 0, 1, 2, 3, 4 or 5, or an addition product thereof with a physiologically acceptable acid or metal salt, which possess fungicidal properties. Intermediates wherein A is a keto group and the azole group is replaced by chloride or bromine are also new.

6 Claims, No Drawings

COMBATING FUNGI WITH TRIAZOLYL-BENZYLOXY-KETONES AND -CARBINOLS

The present invention relates to certain new triazolyl-benzyloxy-ketones and -carbinols, to several processes for their production and to their use as fungicides.

It has already been disclosed that 3,3-dimethyl-1-phenoxy-1-triazolyl-butan-2-ones and -ols which are substituted in the phenyl part, such as 3,3-dimethyl-1-(4-tert.-butylphenoxy)-1-(1,2,4-triazol-1-yl)-butan-2-one or -ol and 3,3-dimethyl-1-(penta-chlorophenoxy)-1-(1,2,4-triazol-1-yl)-butan-2-one, in general have good fungicidal properties (see U.S. Pat. Nos. 3,912,752 and 3,952,002). However, their action is not always completely satisfactory in some fields of application, especially when low amounts and concentrations are applied.

The present invention now provides, as new compounds, the triazolyl-benzyloxy-ketones and -carbinols of the general formula

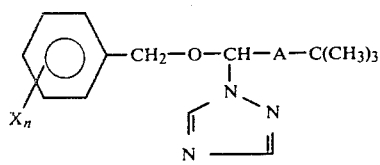

(I)

in which
A represents a keto group or a CH(OH) grouping,
X represents a halogen atom or an alkyl or halogenoalkyl radical and
n is 0, 1, 2, 3, 4 or 5, and physiologically acceptable acid addition salts and metal salt complexes thereof.

Those compounds of the formula (I) in which A represents the CH(OH) group have two asymmetric carbon atoms; they can therefore exist in the two geometric isomer forms (erythro-form and threo-form), which can be obtained in different proportions. In both cases, they are present in the form of optical isomers. All the isomers are claimed according to the invention.

The new triazolyl-benzyloxy-ketones and -carbinols of the present invention have powerful fungicidal properties. Surprisingly, the componds according to the invention exhibit a better fungicidal activity than the compounds 3,3-dimethyl-1-(4-tert.-butyl-phenoxy)-1-(1,2,4-triazol-1-yl)-butan-2-one or -ol and 3,3-dimethyl-1-(pentachlorophenoxy)-1-(1,2,4-triazol-1-yl)-butan-2-one, which are known from the state of the art and are closely related compounds chemically and from the point of view of their action. The substances according to the invention thus represent an enrichment of the art.

Preferred triazolyl-benzyloxy-ketones and -carbinols according to the present invention are those of formula (I) in which X represents a halogen atom, a straight-chain or branched alkyl radical with 1 to 4 carbon atoms or a halogenoalkyl radical with 1 to 2 carbon atoms and 1 to 5 identical or different halogen atoms, such as, preferably fluorine or chlorine atoms, n is 0, 1, 2 or 3 and A has the above-mentioned meaning.

Very particularly preferred compounds of the formula (I) are those in which X represents a fluorine, chlorine or bromine atom or a methyl or trifluoromethyl radical, n is 0, 1 or 2, and A has the above-mentioned meaning.

According to the present invention there is further provided a process for the production of a compound of the present invention, characterized in that (a) a halogenoether-ketone of the general formula

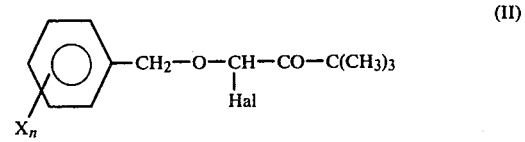

(II)

in which
X and n have the above-mentioned meaning and
Hal represents a chlorine or bromine atom,
is reacted with 1,2,4-triazole in the presence of an acid-binding agent and if appropriate in the presence of a diluent, or (b) a triazolylhalogeno-ketone of the general formula

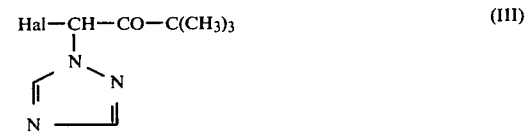

(III)

in which Hal has the above mentioned meaning, is reacted with a benzyl alcohol of the general formula

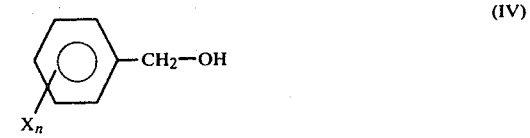

(IV)

in which X and n have the above-mentioned meaning, in the presence of an acid-binding agent and if appropriate in the presence of a diluent, and (c) if appropriate, the keto derivative obtained according to process variant (a) or (b) of the general formula

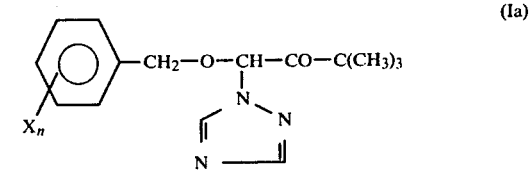

(Ia)

in which X and n have the above-mentioned meaning, is reduced.

If desired, an acid or a metal salt can then be added onto the compounds of the present invention thus obtained.

If, for example, 1-bromo-1-(4-chlorobenzyloxy)-3,3-dimethyl-butan-2-one and 1,2,4-triazole are used as starting substances, the course of process variant (a) is illustrated by the following equation:

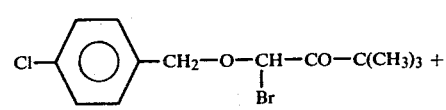

-continued

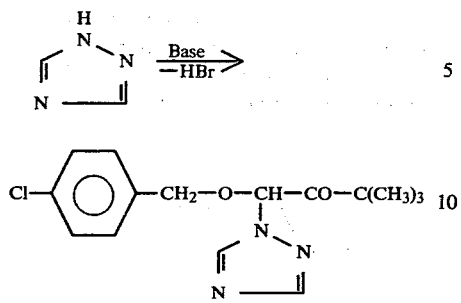

If, for example, 1-bromo-3,3-dimethyl-1-(1,2,4-triazol-1-yl)-butan-2-one and 4-chlorobenzyl alcohol are used as starting substances, the course of process variant (b) is illustrated by the following equation:

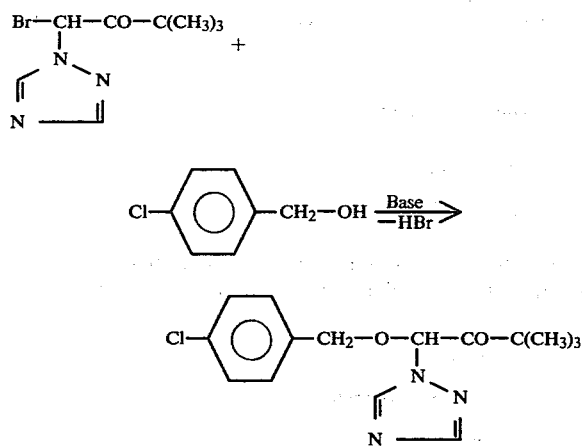

If for example, 1-(4-chlorobenzyloxy)-3,3-dimethyl-1-(1,2,4-triazol-1-yl)-butan-2-one and sodium borohydride are used as starting substances, the course of process variant (c) is illustrated by the following equation:

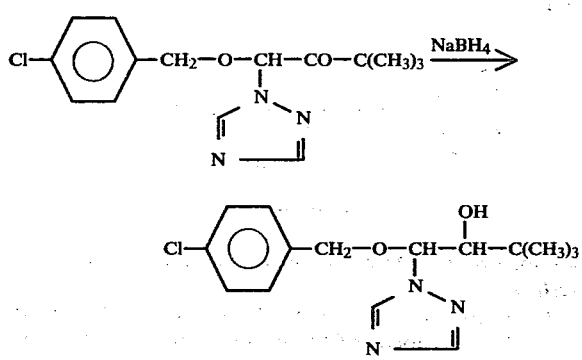

Particularly preferred halogenoether-ketones to be used as starting compounds of formula (II) for process variant (a) are those in which X and n have meanings which have already been mentioned as preferred in connection with the description of the preferred and particularly preferred compounds of the present invention.

The halogenoether-ketones of the formula (II) are novel; however, they can be prepared by known processes, for example by a procedure in which in benzyl ethers of the general formula

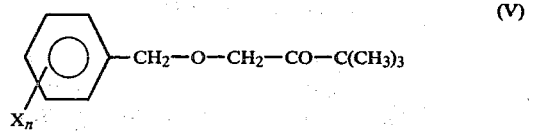

in which X and n have the above-mentioned meaning, one of the two active hydrogen atoms is replaced by chlorine and bromine in the customary manner. The halogenoether-ketones of the formula (II) formed can be further reacted directly, without being isolated (see also the Preparative Examples).

The benzyl ethers of the formula (V) can be obtained by known processes, for example by a procedure in which benzyl alcohols of the formula (IV) are reacted with chloro(bromo)-pinacolin of the formula $$(Br)Cl—CH_2—CO—C(CH_3)_3 \qquad (VI)$$

in the presence of a strong base, such as sodium hydride, and in the presence of an inert organic solvent, such as dimethylformamide, at temperatures between 20° and 100° C.; or by a procedure in which benzyl halides of the general formula

in which Hal, X and n have the above-mentioned meaning, are reacted with hydroxypinacolin of the formula $$HO—CH_2—CO—C(CH_3)_3$$

in a two-phase system, such as aqueous sodium hydroxide solution or potassium hydroxide solution/toluene or methylene chloride, with the addition of a phase transfer catalyst, such as ammonium compounds, for example triethylbenzyl-ammonium chloride.

Triazolylhalogeno-ketones to be used as starting compounds of formula (III) for process variant (b) are known (see U.S. application Ser. No. 964,768, filed Nov. 29, 1978). They are obtained by a procedure in which chloro(bromo)-pinacolin of the formula (VI) is reacted with 1,2,4-triazole in the presence of an acid-binding agent, such as potassium carbonate, and in the presence of an inert organic solvent, such as acetone, at temperatures between 60° and 120° C. One of the two active hydrogen atoms is then replaced by chlorine or bromine in the customary manner.

Particularly preferred benzyl alcohols also to be used as starting componds of formula (IV) for process variant (b) are those in which X and n have meanings which have already been mentioned in connection with the description of the preferred and particularly preferred compounds of the present invention.

The benzyl alcohols of the formula (V) are generally known compounds of organic chemistry.

Possible diluents for the reaction, according to the invention, in process variants (a) and (b) are inert organic solvents. These include, preferably, ketones such as diethyl ketone, and in particular acetone and methyl ethyl ketone, nitriles, such as propionitrile, and in particular acetonitrile; alcohols, such as ethanol or isopropanol; ethers, such as tetrahydrofuran or dioxane; benzene; formamides; such as, in particular, dimethyl formamide; and halogenated hydrocarbons.

The reactions in process variants (a) and (b) are carried out in the presence of an acid-binding agent. It is possible to add all the inorganic or organic acid-binding agents which can customarily be used, such as alkali metal carbonates (for example sodium carbonate, potassium carbonate and sodium bicarbonate), silver carbonate, $C_1$ to $C_4$ tertiary alkylamines, cycloalkylamines, or aralkylamines (for example triethylamine or dimethylbenzylamine) pyridine and diazabicyclooctane.

In process variant (a), it is also possible to use an appropriate excess of the 1,2,4-triazole.

The reaction temperature can be varied within a substantial range in process variants (a) and (b). In general, the reactions are carried out between 20° and 150° C., preferably at 60° to 120° C. If a solvent is present, it is expedient to carry out the reaction at the boiling point of the particular solvent.

In carrying out process variants (a) and (b), 1 to 2 moles of 1,2,4-triazole or 1 to 2 moles of benzyl alcohol of the formula (IV) and in each case 1 to 2 moles of acid binding agent are preferably employed per mole of the compound of the formula (II) or (III). To isolate the compounds of the formula (I), the solvent is distilled off and either water is added to the residue and the mixture is stirred vigorously, whereupon the reaction product crystallizes completely, or the residue is taken up in a mixture of an organic solvent and water and the organic phase is separated off, washed with water, dried over sodium sulphate and freed from the solvent in vacuo. If appropriate, the residue is purified by distillation or recrystallization.

The reduction of process variant (c) is carried out in the customary manner, for example by reaction with complex hydrides, if appropriate in the presence of a diluent, or by reaction with aluminum isopropylate in the presence of a diluent.

If complex hydrides are used, possible diluents for the reaction according to the invention are polar organic solvents. These include, preferably, alcohols, such as methanol, ethanol, butanol and isopropanol, and ethers, such as diethyl ether or tetrahydrofuran. The reaction is in general carried out at 0° to 30° C., preferably at 0° to 20° C. For this reaction, about 1 mole of a complex hydride, such as sodium borohydride or lithium alanate, is employed per mole of the ketone of the formula (Ia). To isolate the reduced compounds of the formula (I), the residue is taken up in dilute hydrochloric acid and the mixture is then rendered alkaline and extracted with an organic solvent. Further working up is carried out in the customary manner.

If aluminum isopropylate is used, preferred possible diluents for the reaction according to the invention are alcohols, such as isopropanol, or inert hydrocarbons, such as benzene. The reaction temperatures can again be varied within a substantial range; in general, the reaction is carried out between 20° and 120° C., preferably 50° to 100° C. For carrying out the reaction, about 1 to 2 moles of aluminum isopropylate are employed per mole of the ketone of the formula (Ia). To isolate the reduced compounds of the formula (I), the excess solvent is removed by distillation in vacuo, and dilute sulphuric acid or sodium hydroxide solution is added to the aluminum compound formed. Further working up is carried out in the customary manner.

The following acids can preferably be used for the preparation of physiologically acceptable acid addition salts of the compounds of the formula (I): hydrogen halide acids (such as hydrobromic acid, and, in particular, hydrochloric acid), phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicylic acid, sorbic acid and lactic acid), and sulphonic acids (such as p-toluenesulphonic acid and 1,5-naphthalenedisulphonic acid). The acid addition salts of the compounds of the formula (I) can be obtained in a simple manner by customary salt formation methods, for example by dissolving a compound of the formula (I) in a suitable inert solvent and adding the acid for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Possible anions of the salts are preferably those which are derived from the following acids: hydrogen halide acids, such as hydrochloric acid and hydrobromic acid, and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be purified in a known manner, for example by filtration, isolation and, if appropriate by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidomycetes, and Deuteromycetes.

The good toleration, by plants, of the active compounds at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as powdery mildew of cereal and powdery mildew of barley; and Venturia species, such as against the apple scab causative organism (*Fusicladium dendriticum*); and for combating powdery mildew of cucumber (*Erysiphe cichoriacearum*). It should be particularly emphasised that the active compounds according to the invention not only have a protective action but also have a systemic action. Thus, it is possible to protect plants from fungal attack if the active compound is fed to the above-ground parts of the plant via the soil and the root or via the seed.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperatures and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillontice or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulpates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules of latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10, are generally required.

For the treatment of soil, active compound concentrations of 0.00001 to 0.1% by weight, preferably 0.0001 to 0.02% are generally required at the place of action.

When applied in appropriate amounts, the compounds according to the invention also exhibit a growth-regulating action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

EXAMPLE 1

(a) (Process variant (a))

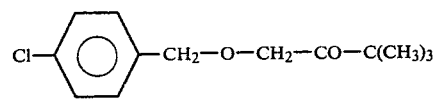
(V-1)

88.8 g (0.6 mole) of 4-chlorobenzyl chloride and 24 g (0.2 mole) of hydroxypinacolin were dissolved in 150 ml of toluene and, after 10 ml of triethyl-benzyl-ammonium chloride and 100 ml of 30% strength sodium hydroxide solution had been added, the mixture was stirred vigorously for 12 hours. The organic phase was then separated off, washed, dried over sodium sulphate and distilled. 33.6 g (70% of theory) of 1-(4-chlorobenzyloxy)-3,3-dimethyl-butan-2-one of boiling point 125° C./0.1 mm Hg were obtained.

The following intermediate products of the general formula

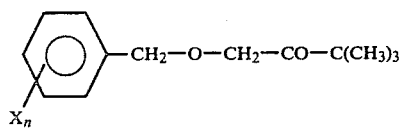

are obtained similarly:

TABLE 1

| Intermediate No. | $X_n$ | Boiling point (°C.)/ mm Hg column |
|---|---|---|
| (V-2) | — | 110/0.9 |
| (V-3) | 3,4-Cl$_2$ | 140/0.1 |
| (V-4) | 2,6-Cl$_2$ | 120/0.1 |

(b) (II-1) 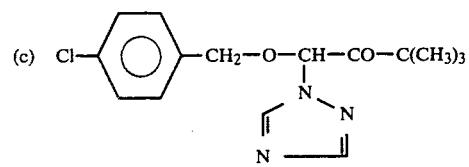

16 g (0.1 mole) of bromine were added to 24 g (0.1 mole) of 1-(4-chlorobenzyloxy)-3,3-dimethyl-butan-2-one in 100 ml of methylene chloride at room temperature in a manner such that continuous decolorization occurred. The reaction mixture was then washed with water and dilute sodium bicarbonate solution, dried over sodium sulphate and concentrated at 40° C. in vacuo by distilling off the solvent. Crude 1-bromo-1-(4-chlorobenzyloxy)-3,3-dimethyl-butan-2-one, which was further reacted directly, was obtained in quantitative yield.

(c) 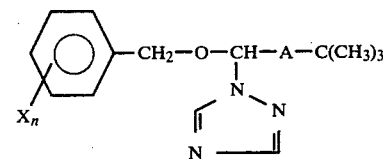 (1)

(Process variant (a))

20.7 g (0.3 mole) of 1,2,4-triazole were added to 31.9 g (0.1 mole) of crude 1-bromo-1-(4-chlorobenzyl)-3,3,-dimethyl-butan-2-one in 100 ml of acetonitrile at room temperature, while stirring. The mixture was stirred under reflux for 1 hour and concentrated by distilling off the solvent and the residue was taken up in methylene chloride/water. The organic phase was separated off, washed again with water, dried over sodium sulphate and concentrated. After purification of the residue by column chromatograph, 12.4 g (45% of theory) 1-(4-chlorobenzyloxy)-3,3-dimethyl-1-(1,2,4-triazol-1-yl)-butan-2-one were obtained as a viscous oil.

EXAMPLE 2

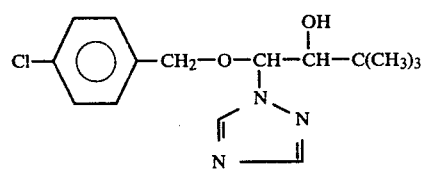

(Process variant (c))

3.8 g (0.1 mole) of sodium borohydride were added to 30.7 g (0.1 mole) of 1-(4-chlorobenzyloxy)-3,3-dimethyl-1-(1,2,4-triazol-1-yl)-butan-2-one (obtained as described in Example 1) in 200 ml of ethanol at room temperature, while stirring. As soon as the exothermic reaction had subsided, the reaction mixture was heated to 60° C. for 1 hour. It was then concentrated and the residue was partitioned between methylene chloride and water. The organic phase was separated off, washed with water, dried over sodium sulphate and concentrated. After pre-purification of the residue by column chromatography, the product was recrystallized from cyclohexane. 15.4 g (50% of theory) of 1-(4-chloro-benzyl)-3,3-dimethyl-1-(1,2,4-triazol-1-yl)-butan-2-ol of melting point 96° C. were obtained.

The following compounds of the general formula

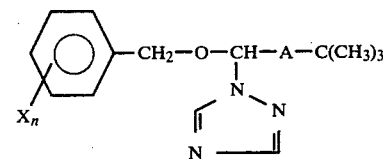

were obtained analogously:

| Compound No. | $X_n$ | A | Melting point (°C.) |
|---|---|---|---|
| 3 | — | CO | 43 to 48 |
| 4 | 3,4-Cl$_2$ | CO | 97 |
| 5 | 2,6-Cl$_2$ | CO | 119 |
| 6 | — | CH(OH) | 74 |
| 7 | 3,4-Cl$_2$ | CH(OH) | 55 to 61 |
| 8 | 2,6-Cl$_2$ | CH(OH) | 125 |

The fungicidal activity of the compounds of this invention is illustrated by the following examples wherein the compounds according to the present invention are each identified by the number (given in brackets) from the preparative examples hereinabove:

(A) = 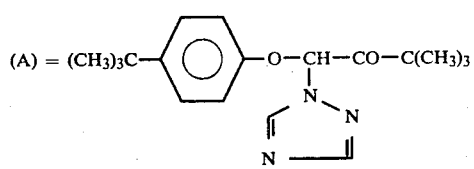

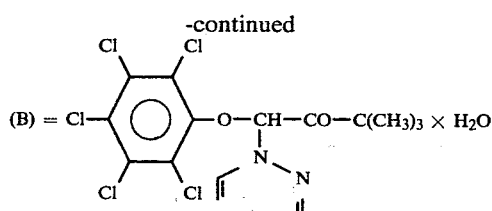

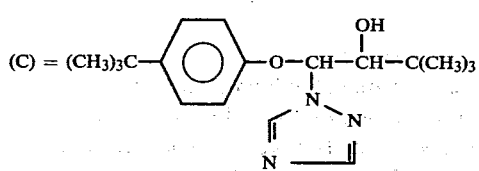

EXAMPLE 3

Shoot treatment test/powdery mildew of cereal/protective (leaf-destructive mycosis)

To produce a suitable preparation of active compound 0.25 part by weight of active compound was taken up in 25 parts by weight of dimethylformamide and 0.06 part by weight of emulsifier (alkylaryl polyglycol ether), and 975 parts by weight of water were added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of Erysiphe graminis var. hordei.

After 6 days' dwell time of the plants at a temperature of 21° to 22° C. and 80 to 90% atmospheric humidity, the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

In this test, for example, the following compounds exhibited a very good action which was superior to that of the compounds (A) and (B) known from the prior art: compounds (6), (2), (7), (3), (4), (1), (5).

TABLE 2

| Shoot treatment test/powdery mildew of cereal/protective | | |
|---|---|---|
| Active Compounds | Concentration active compound in the spray liquor in % by weight | Infection in % of the untreated control |
| (A) (known) | 0.01 | 82.5 |
| (B) (known) | 0.01 | 91.3 |
| (6) | 0.01 | 15.0 |
| (2) | 0.025 | 0.0 |
|  | 0.0025 | 15.0 |
| (7) | 0.025 | 0.0 |
|  | 0.0025 | 12.5 |
| (3) | 0.01 | 48.8 |
| (4) | 0.01 | 0.0 |
| (1) | 0.01 | 5.0 |
| (5) | 0.01 | 15.0 |

EXAMPLE 4

Powdery mildew of barley test (Erysiphe graminis var. hordei)/systemic (fungal disease of cereal shoots)

The active compounds were used as pulverulent seed treatment agents. These were produced by extending the active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had unfolded their first leaf, they were dusted with fresh spores of Erysiphe graminis var. hordei and grown on at 21°–22° C. and 80–90% relative atmospheric humidity and 16 hours' exposure to light. The typical mildew pustules formed on the leaves within 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

In this test, for example, the following compounds exhibited a very good action which was superior to that of the compounds (A) and (C) known from the prior art: compounds (6), (2), (7), (3) and (4).

TABLE 3

| Powdery mildew test (Erysiphe graminis var. hordei)/systemic | | | |
|---|---|---|---|
| Active compounds | Active compound concentration in the dressing agent in % by weight | Amount of dressing agent applied in g/kg of seed | Infection in % of the untreated control |
| (C) (known) | 25 | 10 | 100 |
| (A) (known) | 25 | 10 | 100 |
| (6) | 25 | 10 | 0.0 |
| (2) | 25 | 10 | 3.8 |
| (7) | 25 | 10 | 0.0 |
| (3) | 25 | 10 | 12.5 |
| (4) | 25 | 10 | 0.0 |

It will be understood that the specification and examples are illustrative but not limitative of the present invention and that other embodiments within the spirit and scope of the invention will suggest themselves to those skilled in the art.

We claim:

1. A triazolyl-benzyloxy-ketone or carbinol of the formula

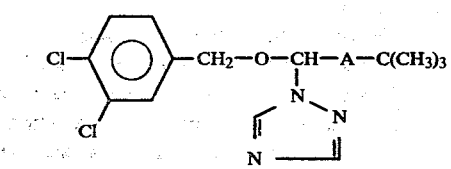

in which A is a keto group or a CH(OH) group, or an addition product thereof with a physiologically acceptable acid or metal salt.

2. A compound according to claim 1, wherein such compound is 1-(3,4-dichlorobenzyloxy)-3,3-dimethyl-1-(1,2,4-triazol-1-yl)-butan-2-one of the formula

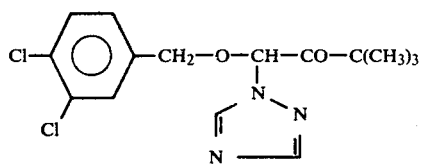

or an addition product thereof with a physiologically acceptable acid or a metal salt.

3. A compound according to claim 1, wherein such compound is 1-(3,4-dichlorobenzyloxy)-3,3-dimethyl-1-(1,2,4-triazol-1-yl)-butan-2-ol of the formula

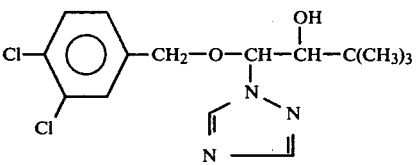

or an addition product thereof with a physiologically acceptable acid or a metal salt.

4. A fungicidal composition comprising a fungicidally effective amount of a compound according to claim 1 in admixture with a diluent.

5. A method of fungi comprising applying to the fungi or to a habitat thereof a fungicidally effective amount of a compound according to claim 1.

6. The method according to claim 5, wherein such compound is
1-(3,4-dichlorobenzyloxy)-3,3-dimethyl-1-(1,2,4-triazol-1-yl)-butan-2-one,
1-(3,4-dichlorobenzyloxy)-3,3-dimethyl-1-(1,2,4-triazol-1-yl)-butan-2-ol,
or an addition product thereof with a physiologically acceptable acid or a metal salt.

* * * * *